United States Patent
Eifrig

(10) Patent No.: US 6,244,267 B1
(45) Date of Patent: Jun. 12, 2001

(54) RESPIRATOR WITH A PRESSURE RELIEF VALVE

(75) Inventor: Reinhard Eifrig, Lübeck (DE)

(73) Assignee: Dräger Medizintechnick GmbH (DE)

( * ) Notice: Subject to any disclaimer, the term of this patent is extended or adjusted under 35 U.S.C. 154(b) by 0 days.

(21) Appl. No.: 09/546,649

(22) Filed: Apr. 10, 2000

(30) Foreign Application Priority Data

Jul. 8, 1999 (DE) .............................................. 199 31 807

(51) Int. Cl.[7] .................................................. A61M 16/00
(52) U.S. Cl. .............................. 128/202.22; 128/205.24; 128/204.26
(58) Field of Search ................. 128/202.22, 204.24, 128/204.26, 204.18, 204.21, 205.24

(56) References Cited

U.S. PATENT DOCUMENTS

| | | | | |
|---|---|---|---|---|
| 3,831,596 | * | 8/1974 | Cavallo | 128/205.24 |
| 3,949,749 | * | 4/1976 | Stewart | 128/204.24 |
| 4,227,523 | * | 10/1980 | Warnow et al. | 128/204.24 |
| 4,350,115 | * | 9/1982 | Pasternack | 128/202.22 |
| 4,466,433 | * | 8/1984 | Robbins | 128/205.24 |
| 4,611,591 | * | 9/1986 | Inui et al. | 128/204.21 |
| 4,838,257 | * | 6/1989 | Hatch | 128/205.24 |
| 5,596,984 | * | 1/1997 | O'Mahony et al. | 128/205.24 |
| 5,797,393 | * | 8/1998 | Kohl | 128/204.23 |
| 5,813,399 | * | 9/1998 | Isaza et al. | 128/205.24 |

FOREIGN PATENT DOCUMENTS

| 28 01 546 C2 | 7/1979 | (DE) . |
|---|---|---|
| 195 16 536 C2 | 11/1996 | (DE) . |

* cited by examiner

*Primary Examiner*—Aaron J. Lewis
(74) *Attorney, Agent, or Firm*—McGlew & Tuttle, P.C.

(57) ABSTRACT

A respirator with an inhalation line (3), an exhalation line (5) with an exhalation valve (6), with a pressure-measuring device (8) for measuring the airway pressure, and with a circuit (7) for controlling the phases of breathing. The circuit is connected at least to the exhalation valve (6). A rapid reduction in pressure in the breathing gas lines (3, 5) is possible at any time using a control valve (10) in the inhalation line (3) provided with a control pressure space (15) and with a discharge port (19) which can be opened to the environment through a valve element (14). A control pressure line (16), which is branched off from the inhalation line (3) and can be connected to the control pressure space (15), is present. A reversing valve (17) with an evacuation line (18), through which a flow connection can be established between the control pressure space (15) and the evacuation line (18), is arranged in the control pressure line (16).

7 Claims, 1 Drawing Sheet

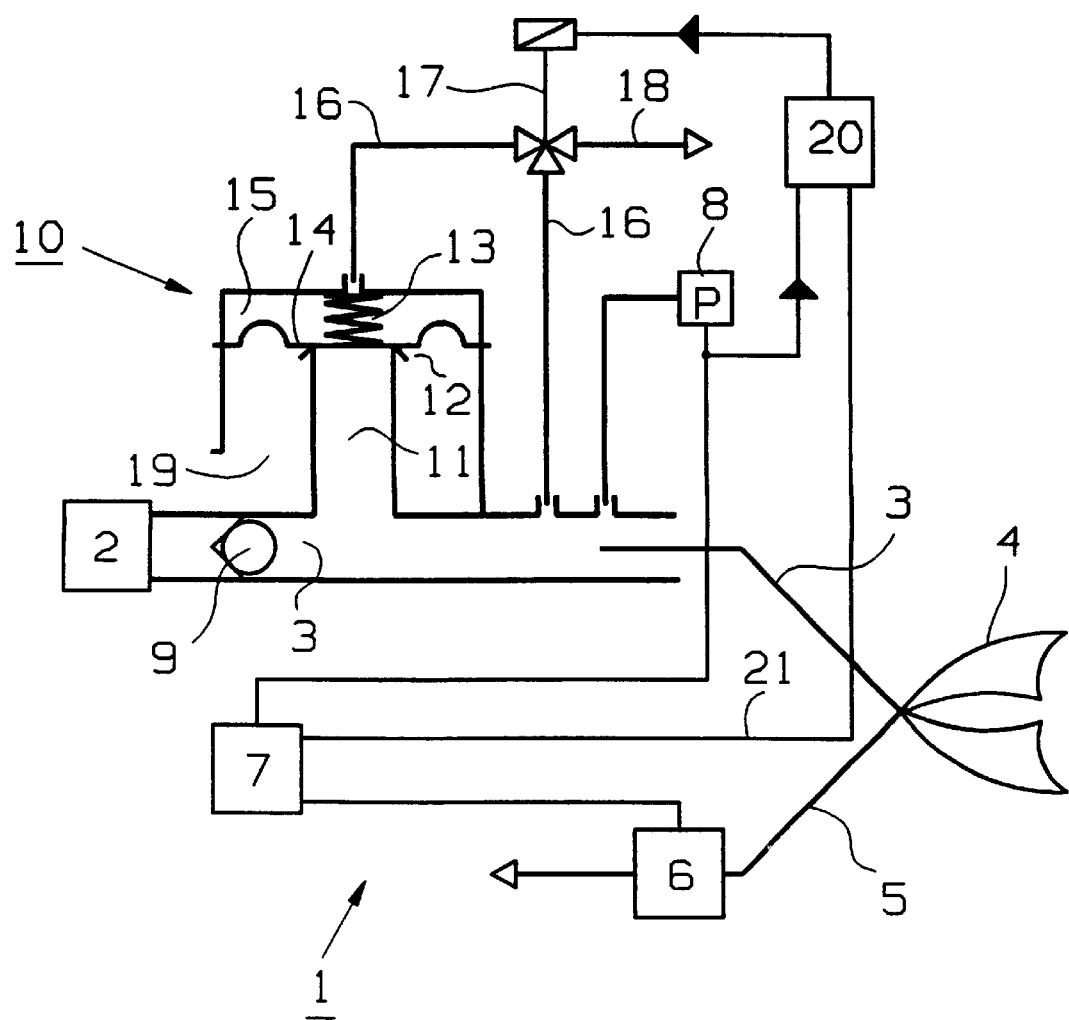

RESPIRATOR WITH A PRESSURE RELIEF VALVE

FIELD OF THE INVENTION

The present invention pertains to a respirator with an inhalation line, a exhalation line with an exhalation valve, a pressure-measuring means for measuring the airway pressure p and with a circuit connected at least to said exhalation valve for controlling the phases of respiration.

BACKGROUND OF THE INVENTION

A respirator with an inhalation line, an exhalation line, a metering means for inhaled gas, as well as an exhalation valve that can be actuated has been known from DE 195 16 536 C2, with which both a volume-controlled and pressure-controlled respiration can be performed. Both the breathing gas flow and the breathing gas pressure are monitored during the respiration. A stenosis and disconnection alarm device as well as a pressure relief valve are usually present as safety and monitoring means. The pressure relief valve is used to reduce excess pressure during the inhalation phase and to limit them to a predetermined limit value. A pressure-limiting valve of this type is shown as an example in DE 28 01 546 C2.

An excessively high respiration pressure may have various causes. For example, the breathing gas flow is set to an excessively high value or the inhalation tube leading to the patient is kinked. However, cases of application in which a rapid pressure relief of the breathing gas-carrying components must be performed are also conceivable, e.g., in the case of the sudden onset of spontaneous respiratory activity or cough-related gasps. An overpressure limitation alone is not sufficient in these cases. On the other hand, it must also be ensured that the patient can exhale at any time. Exhalation via the exhalation valve is no longer possible in the case of a partially or completely kinked exhalation tube, and the pressure relief valve remains closed until the maximum pressure set is reached.

SUMMARY AND OBJECTS OF THE INVENTION

The primary object of the present invention is to improve a respirator of the type such that a rapid pressure reduction can be established in the breathing gas lines leading to the patient.

According to the invention, a respirator is provided with an inhalation line an exhalation line with an exhalation valve, a pressure-measuring means for measuring the airway pressure p and with a circuit connected at least to the exhalation valve for controlling the phases of respiration. A control valve is provided in the inhalation line with a control pressure space and with a discharge port. The discharge port can be opened to the environment through a said valve element. A control pressure line, which is branched off from the inhalation line and can be connected to the control pressure space is also provided. A reversing valve with an evacuation line, through which a flow connection can be established between the control pressure space and the evacuation line, is arranged in the control pressure line.

The advantage of the present invention is essentially that a rapid pressure relief of the components carrying breathing gas is possible through the control valve arranged in the inhalation line at both a high inhalation pressure and increased exhalation resistance, e.g., as a consequence of a kinked exhalation line. However, the exceeding of permissible pressure limits may also be caused by the patient's spontaneous breathing activity. By opening the control valve, the patient has the possibility at any time during the inhalation phase and the exhalation phase to release the exhaled gas directly into the environment via the control valve or to obtain inhaled gas via the control valve. Diaphragm valves, in which the valve element is designed as an elastic diaphragm, are especially suitable as control valves.

It is particularly advantageous to connect the pressure-measuring means to a limit value transducer, which compares the instantaneously measured airway pressure p with a limit pressure $p_g$ and sends a reversing signal to the reversing valve when the limit value is exceeded. The reversing valve is actuated by the reversing signal such that a flow connection is established between the control pressure space and the evacuation line, through which the pressure in the control pressure space is reduced to the ambient pressure level and the control valve opens.

An especially good pressure monitoring is possible if different limit valves $p_{g1}$ and $p_{g2}$ are preset as the limit pressure $p_g$ during the inhalation phase and the exhalation phase.

The various features of novelty which characterize the invention are pointed out with particularity in the claims annexed to and forming a part of this disclosure. For a better understanding of the invention, its operating advantages and specific objects attained by its uses, reference is made to the accompanying drawing and descriptive matter in which a preferred embodiment of the invention is illustrated.

BRIEF DESCRIPTION OF THE DRAWING

In the drawing:

The only FIGURE is a schematic view of a respirator according to the invention.

DESCRIPTION OF THE PREFERRED EMBODIMENT

Referring to the drawing in particular, the only FIGURE schematically shows a respirator 1, in which a breathing gas-metering means or breathing gas-metering device 2 delivers breathing gas via an inhalation line 3 to a patient 4 and exhaled breathing gas is removed via an exhalation line 5 and an exhalation valve 6. The phases of respiration are controlled by a logic circuit 7, which is connected to both the breathing gas-metering means 2 and the exhalation valve 6. The exhalation valve 6 is closed during the phase of inhalation, so that the inhalation pressure, which is measured by means of a pressure-measuring means 8 located in the inhalation line 3, can build up in the inhalation line 3. Downstream of a nonreturn valve 9, a control valve 10 is provided. The control valve 10 comprises a valve port 11 branched off from the inhalation line 3 with the valve seat 12 and a diaphragm 14. The diaphragm 14 lies on the valve seat 12 and is pressed on by a spring 13. The control valve 10 is also located in the inhalation line 3. On the side of the diaphragm 14 facing away from the valve port 11 there is located a control pressure space 15. The control pressure space 15 is connected to the inhalation line 3 via a control pressure line 16 and a reversing valve 17. The respiration pressure is admitted to the control pressure space 15 via the control pressure line 16, and the diaphragm 14 is pressed against the valve seat 12. An evacuation line 18 is branched off from the reversing valve 17. The evacuation line 18 is closed in a first switching position of the reversing valve 17 and is connected to the control pressure space 15 via the control pressure line 16 in a second switching position of the reversing valve 17. In this second switching position of the reversing valve 17 the pressure in the control pressure space 15 is reduced to the ambient pressure level and the diaphragm 14 lifts off from the valve seat 12. The breathing gas present in the inhalation line 3 and in the patient 4 can flow off into the environment via the valve seat 12 and a discharge port 19 with the pressure relieved on the diaphragm 14.

The reversing valve 17 is actuated by a limit value transducer 20, which is connected to the pressure-measuring means 8, which compares the instantaneous pressure p prevailing in the inhalation line 3 with a limit pressure $p_g$ and sends a control signal to the reversing valve 17 when the limit pressure $p_g$ is exceeded. The flow connection is established by the control signal between the control pressure space 15 and the evacuation line 18. The limit value transducer 20 is connected to the circuit 7 via a signal line 21, by which the limit value transducer 20 can be activated or deactivated and receives preset values for the limit pressure $p_g$.

The respirator 1 according to the present invention operates as follows.

During the phase of inhalation, the inhalation pressure is built up in the inhalation line 3, so that the breathing gas volume delivered by the breathing gas-metering unit 2 is delivered into the lungs of the patient 4. The limit pressure $p_{g1}$, which is transmitted via the signal line 21 to the limit value transducer 20, is set as the maximum inhalation pressure on the circuit 7. As long as the instantaneous inhalation pressure p is lower than $p_{g1}$, the reversing valve 17 is in a switching position in which the control pressure space 15 is connected to the inhalation line 3 via the control pressure line 16, so that the valve port 11 is closed by the diaphragm 14. If the breathing pressure p exceeds the limit value $p_{g1}$, the reversing valve 17 receives from the limit value transducer 20 a control signal, by which the control pressure space 15 is connected to the evacuation line 18 and the pressure in the control pressure space 15 is reduced to the ambient pressure level. The diaphragm 14 will then be lifted off from the valve crater or valve seat 12 and the breathing gas present in the inhalation line 3 can escape via the discharge port 19. With the control valve 10 open, the patient 4 can also obtain the breathing gas needed for the spontaneous breathing activity via the discharge opening 19.

The supply of breathing gas through the breathing gas-metering unit 2 is interrupted and the exhalation valve 6 is opened during the exhalation phase. The exhalation valve 6 limits the exhalation pressure to the so-called end-expiratory pressure. This value is entered as a second limit value $p_{g2}$ in the limit value transducer 20 via the circuit 7 and the signal line 21 during the exhalation phase and a comparison with the instantaneous exhalation pressure p is performed in the limit value transducer. If the limit value is exceeded, which may be due, e.g., to a kinked exhalation tube 5, the reversing valve 17 switches over into the second switching position, and the evacuation line 18 is in flow connection with the control pressure space 15, so that the control valve 10 opens and the patient 4 can exhale via the valve port 11 and the discharge opening 19. Improved monitoring of respiration and an immediate pressure relief of the inhalation line 3 and exhalation line 5 are possible during the entire phase of breathing due to the individual preset limit values during the inhalation phase and the exhalation phase and due to the opening of the control valve 10 when the limit value is exceeded.

While a specific embodiment of the invention has been shown and described in detail to illustrate the application of the principles of the invention, it will be understood that the invention may be embodied otherwise without departing from such principles.

What is claimed is:

1. A respirator, comprising:

an inhalation line;

an exhalation line;

an exhalation valve connected to said exhalation line;

a pressure-measuring device for measuring the airway pressure;

an electrical circuit connected to said exhalation valve for controlling the phases of respiration;

a control valve with a control pressure space and with a discharge port having a valve element, said discharge port being opened to the environment through said valve element, said control valve being connected to said inhalation line;

a control pressure line branched off from said inhalation line, said control pressure line being connected to said control pressure space;

an evacuation line; and a reversing valve connected to said evacuation line and connected to said control pressure line, said reversing valve for selectively establishing a flow connection between said control pressure space and said evacuation line and for selectively establishing a flow connection between said control pressure space and said inhalation line via said control pressure line.

2. A respirator in accordance with claim 1, further comprising: a limit value transducer, wherein said pressure-measuring device is connected to said limit value transducer, said limit value transducer being designed to send a reversing signal to said reversing valve when a limit value of the airway pressure is exceeded, where the airway pressure is greater than or equal to a limit pressure, and a flow connection is established between said control pressure space and said evacuation line.

3. A respirator in accordance with claim 2, wherein different limit values $pg_{g1}$, $p_{g2}$ are present at said limit value transducer during an inhalation phase and during an exhalation phase.

4. A respirator, comprising:

an inhalation line;

an exhalation line;

an exhalation valve connected to said exhalation line;

a pressure-measuring means for measuring the airway pressure;

an electrical circuit connected at least to said exhalation valve for controlling the phases of respiration;

a control valve with a control pressure space and with a discharge port having a valve element, said discharge port being opened to the environment through said valve element, said control valve being provided in said inhalation line;

a control pressure line branched off from said inhalation line, said control pressure line being connected to said control pressure space;

an evacuation line; and a reversing valve provided in said control pressure line and connected to said evacuation line, said reversing valve for selectively establishing a flow connection between said control pressure space and said evacuation line and for selectively establishing a flow connection between said control pressure space and said inhalation line via said control pressure line.

5. A respirator in accordance with claim 4, further comprising: a limit value transducer, wherein said pressure-measuring device is connected to said limit value transducer, said limit value transducer being designed to send a reversing signal to said reversing valve when a limit value of the airway pressure is exceeded, where the airway pressure is greater than or equal to a limit pressure, and a flow connection is established between said control pressure space and said evacuation line.

6. A respirator in accordance with claim 5, wherein different limit values $p_{g1}$, $p_{g2}$ are present at said limit value transducer during an inhalation phase and during an exhalation phase.

7. A respirator in accordance with claim 4, further comprising: a limit value transducer, wherein said pressure-measuring device is connected to said limit value transducer, said limit value transducer being designed to send a reversing signal to said reversing valve when a limit value of the airway pressure is exceeded, said limit value being a value during an inhalation phase and being another value during an exhalation phase.

* * * * *